(12) United States Patent
Matsui et al.

(10) Patent No.: US 7,475,411 B2
(45) Date of Patent: Jan. 6, 2009

(54) CLEANER UTILIZING ADHESIVE MEMBER, AND OPTICAL INFORMATION PROCESSING DEVICE INCORPORATING THE SAME

(75) Inventors: Kiyoto Matsui, Kawasaki (JP); Tohru Fujimaki, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 163 days.

(21) Appl. No.: 11/104,526

(22) Filed: Apr. 13, 2005

(65) Prior Publication Data

US 2005/0174693 A1 Aug. 11, 2005

Related U.S. Application Data

(63) Continuation of application No. PCT/JP03/00441, filed on Jan. 20, 2003.

(51) Int. Cl.
*G11B 33/14* (2006.01)
(52) U.S. Cl. .................................... 720/648
(58) Field of Classification Search ............ 720/648
See application file for complete search history.

(56) References Cited

U.S. PATENT DOCUMENTS 6,157,605 A * 12/2000 Mori ........................ 720/648

2005/0055705 A1 * 3/2005 Fritsch et al. ............... 720/671

FOREIGN PATENT DOCUMENTS

| JP | 1-251483 | 10/1989 |
|---|---|---|
| JP | 3-58331 | 3/1991 |
| JP | 4-221432 | 8/1992 |
| JP | 5-120713 | 5/1993 |
| JP | 06-084275 | 3/1994 |
| JP | 6-124473 | 5/1994 |
| JP | 8-55356 | 2/1996 |
| JP | 2000-251296 | 9/2000 |
| JP | 2002-367338 | 12/2002 |

OTHER PUBLICATIONS

Office Action mailed from the Japanese Patent Office on Oct. 9, 2007.

* cited by examiner

*Primary Examiner*—David D Davis
(74) *Attorney, Agent, or Firm*—Staas & Halsey LLP

(57) ABSTRACT

A cleaner ($C_1$) for an magneto-optical disk device includes a cartridge (4), a disk (1), an adhesive sheet (2) stuck to the disk (1), a clamping disk (3), and a shutter (5). The clamping disk (3) is stored rotatable in the cartridge (4), and the disk (1) is fixed to the cartridge (4) at a position apart from the clamping disk (3). By this means, it becomes possible to safely clean an optical head (17). Also, dust can be prevented from scattering to the magneto-optical disk device ($P_1$).

9 Claims, 6 Drawing Sheets

CLEANER UTILIZING ADHESIVE MEMBER, AND OPTICAL INFORMATION PROCESSING DEVICE INCORPORATING THE SAME

This application is a continuing application, filed under 35 U.S.C. §111(a), of International Application PCT/JP2003/000441, filed Jan. 20, 2003.

TECHNICAL FIELD

The present invention relates to a cleaner for cleaning an optical head of an optical information processing device and an optical information processing device.

The "optical information processing device" in this specification refers to an information processing device which can record and/or playback data employing an optical means. Hence, it is a broad concept which includes a type of information processing device which can perform data rewriting to an optical recording medium by the magneto-optical recording method or the phase change method in additional to an optical processing device of a narrow definition dedicated to reading data from an optical disk.

BACKGROUND ART

In optical disk devices represented by CD players and DVD players, reading/writing of information to an optical disk is performed using an optical head. The optical head is equipped with an objective lens which forms a laser spot on the recording plane of an optical disk by condensing laser light emanating from a laser light source. Dust may adhere to the objective lens, which if it becomes dirty, the reading/writing performance of the optical head becomes degraded. Hence, it is desirable that the optical head be cleaned periodically, and various kinds of cleaners have been proposed in the past as stated hereafter.

Described in JP-A-2000-251296 is a cleaner for optical disk devices. The cleaner has a brush installed on a disk. By inserting the cleaner to an optical disk device and placing the brush in contact with the optical head of the optical disk device in a state where the disk is rotated at high speed, cleaning of the optical disk is performed.

Described in JP-A-H4-221432, H5-120713, H6-124473, and H8-55356 are cleaners which use a cloth, a wet-type tip, an elastically-deformable porous body, or a spongy elastic member as a contact member for cleaning an optical head. In the cleaners described in these laid-open patent publications as well, in the same way as for the cleaner described in JP2000-251296, cleaning the optical head is performed by putting the contact member in contact with the optical head while rotating it at high speed.

However, in these prior-art techniques, because the contact member is brought into contact with the optical head while rotating it at high speed, there is the possibility that the objective lens of the optical head may be scratched. Also, dust attached to the optical head will be scattered into the optical information processing device by the high-speed rotation of the contact member. Hence, there is also the problem that dust remains and accumulates inside the optical disk device.

DISCLOSURE OF THE INVENTION

The objective of the present invention is to provide a cleaner for an optical information processing device and an optical information processing device which can solve or reduce the problem.

The cleaner for optical information processing devices provided by the first aspect of the present invention is a cleaner for optical processing devices equipped with a contact member for cleaning which can come into contact with the optical head of an optical information processing device and is characterized by the fact that an adhesive member having adhesive on its surface is used as the contact member.

Preferably, the adhesive member should be constructed to maintain a state wherein movement intersecting with its contact direction is prevented when it comes into contact with the optical head.

Preferably, at least the surface portion of the adhesive member is provided with rubbery elasticity.

Preferably, at least the surface portion of the adhesive member is constructed of a gel.

Preferably, as the optical recording medium of an optical information processing device, the cleaner for the optical information processing devices of the present invention is equipped with a cartridge which is loadable to the loading section, wherein the adhesive member is contained within the cartridge, and a window is formed which enables contact between the adhesive member and the optical head.

Preferably, the cleaner for optical information processing devices of the present invention is equipped with a shutter which enables the window to open/close freely.

Preferably, the adhesive member is installed on the position inside the cartridge facing the window.

Preferably, a disk for clamping is contained to be rotatable inside the cartridge, and the adhesive member should be positioned in a place apart from the disk.

Preferably, it is equipped with a first disk for clamping, and a second disk supported by the first disk, and is provided with a built-in adhesive member, wherein the first and second disks is allowed to rotate relative to each other in the track direction.

Preferably, a hole for spindle insertion is formed on the center of the first disk.

Preferably, a hole is formed on the center of the second disk, and the whole or a part of the first disk is fit into the hole in a relatively rotatable manner.

Preferably, a support means is built into the optical information processing device and supports the adhesive member. At least one of the optical head and the support means is movable in the focusing direction and a direction intersecting with the focusing direction, whereby the optical head and the adhesive member are brought into contact with each other and brought away from each other.

An optical information processing device according to a second aspect of the present invention includes an optical head and a cleaning contact member that can be brought into contact with the optical head. The contact member comprises an adhesive member having an adhesive surface.

The characteristics and advantages of the present invention will become clear from the explanations of the embodiments of the present invention stated below.

BEST MODE FOR CARRYING OUT THE INVENTION

Preferred embodiment forms of the present invention are explained hereafter with reference to the drawings.

Figure 1:
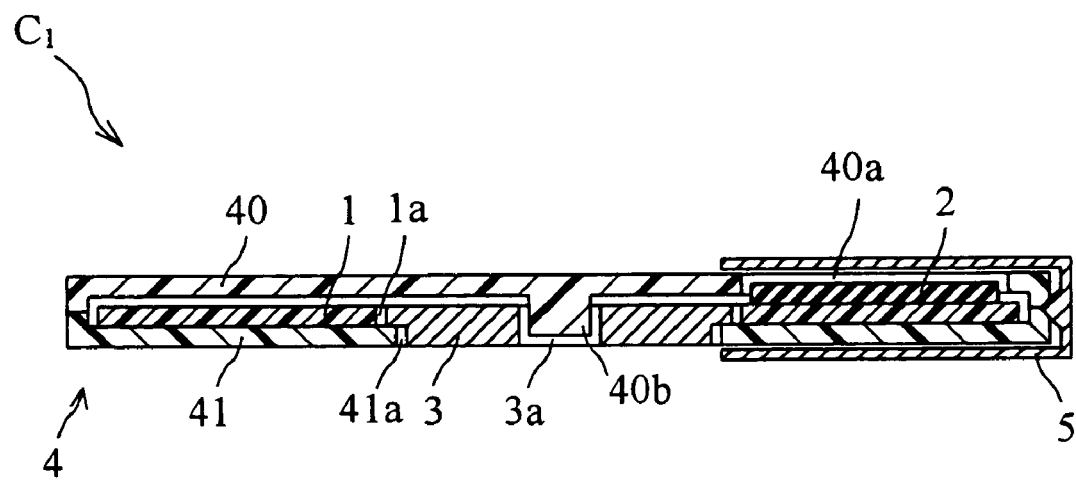
FIG. 1 is a cross-sectional view of an example of the cleaner for optical information processing devices related to the present invention.
Figure 2:
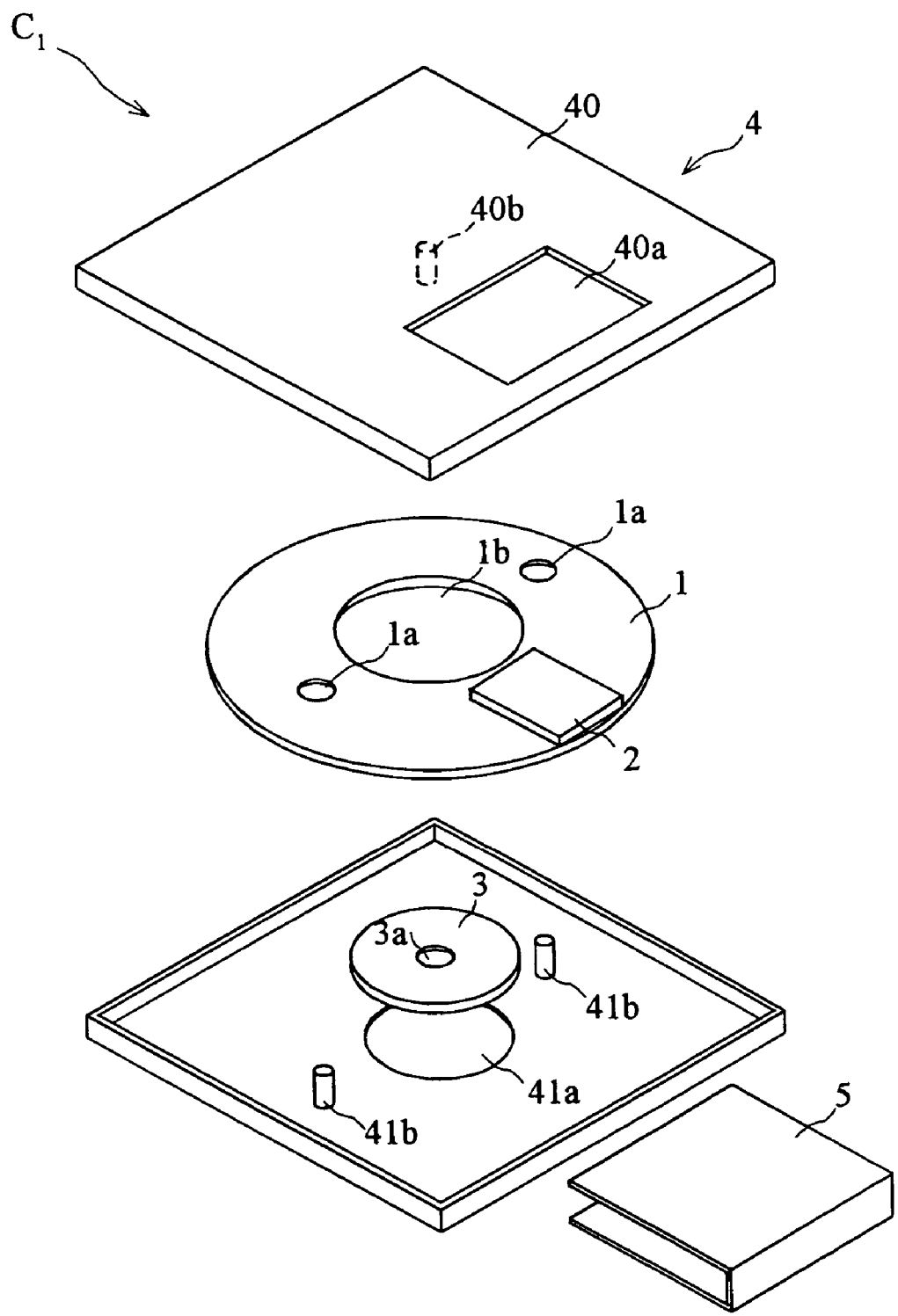
FIG. 2 is an exploded oblique view of the cleaner for optical information processing devices shown in FIG. 1.

FIGS. 1 and 2 show an example of the cleaner for optical information processing devices to which the present invention is applied. A cleaner $C_1$ is used for cleaning magneto-optical disk devices is constructed to be equipped with a cartridge 4, a disk 1 contained in the cartridge 4, an adhesive sheet 2, a clamping disk 3, and a shutter 5.

The cartridge 4 is formed by joining a first member 40 and a second member 41 so as to form a apace inside. A window 40a is formed on the first member 40. Attached to the center inside the cartridge 4 is the clamping disk 3 which is rotated by a spindle 20 of a magneto-optical disk device $P_1$ shown in FIG. 3. Formed on the center of the second member 41 is a circular opening 41a which exposes one side of the clamping disk 3 to allow the spindle of the magneto-optical disk device $P_1$ to make contact. The shutter 5 is for opening/closing the window 40a and ordinarily keeps the window 40a closed with a force of a spring (not shown). On the other hand, when the cleaner $C_1$ is loaded into the magneto-optical disk device $P_1$, this shutter 5 moves by a shutter opening mechanism of the magneto-optical disk $P_1$ and opens the window 40a.

The adhesive sheet 2 is pasted on the position facing the window 40a on one side of the disk 1. As the adhesive sheet 2, use is made of one made of a material equipped with enough adhesiveness to effectively attach dust on its surface. However, materials having excessive adhesiveness are not appropriate because the adhesive component would stick to an optical head 17 of the magneto-optical disk device $P_1$. The entire adhesive sheet 2 has rubbery elasticity, and is made of silicone rubber as its concrete material. As material equipped with such requirements as the above and which are in wide circulation, there are KE3495 manufactured by Shin'etsu Chemical Industry Corp. and SRT-33-S manufactured by Sakase Chemical Industry Corp. for example. Specifically, the adhesive sheet 2 may be given construction wherein it is entirely made of silicone rubber and pasted to the disk 1 with an adhesive, etc. The present invention also allows construction which employs a sheet wherein only the surface portion is made of silicone rubber, in which an adhesive layer is formed on the other face, and they are accumulated with a base substance.

The disk 1 has an opening 1a on the center, and its shape and size in the state where the clamping disk 3 is combined with it are similar to those of general cartridge-type magneto-optical disks. This disk 1 is fixed to the second member 41 by the opening 1a installed on the disk 1 and a pin 41b installed on the second member 41 of the cartridge, fitting with one another. On the other hand, the clamping disk 3 is rotatably supported by the first member 40 and the second member 41 of the cartridge 4. In the example shown in FIG. 1, a pin 40b installed on the first member 40 is inserted into an opening 3a installed on the clamping disk 3, and the clamping disk 3 is supported to be freely rotatable inside the disk 1 by being sandwiched by the first member 40 and the second member 41. According to such construction, when the cleaner $C_1$ is loaded into the magneto-optical disk device $P_1$, only the clamping disk 3 is rotated by the spindle of the magneto-optical disk device $P_1$, and the disk 1 is not rotated.

Figure 3:
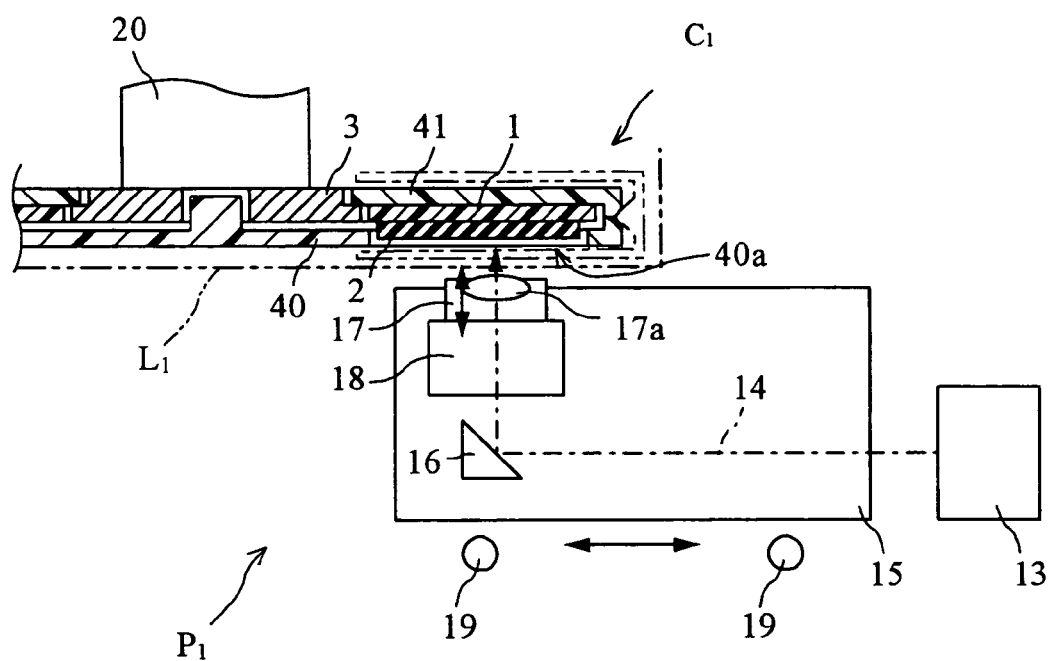
FIG. 3 is an explanatory drawing of the state of using the cleaner for optical information processing devices shown in FIG. 1.

An explanation is provided next of the construction of the magneto-optical disk device $P_1$ wherein the cleaner $C_1$ is used, with reference to FIG. 3.

The magneto-optical disk device $P_1$ is equipped with an optical unit 13, a carriage 15, and a spindle 20. The optical unit 13 is equipped with an light emission system comprising a laser light source, a prism to form light, etc., and a light reception system comprising a beam splitter to split light returned from an optical disk, a detector to sense returned light, a lens to condense light onto the detector, etc. (none of them shown). A laser beam 14 emitted from the optical unit 13 is changed of its direction toward the disk 1 by an upward-redirecting mirror 16 of the carriage 15. The laser beam 14 passes through an objective lens 17a installed on an optical head 17 and is radiated onto an magneto-optical disk (not shown) loaded in a loading section $L_1$. (Shown in FIG. 3 is a state in which the cleaner $C_1$ is loaded, and the magneto-optical disk is not shown.) The carriage 15 is equipped with a bearing 19, which is made to be movable in the radial direction of the disk 1. The optical head 17 is supported by a suspension (not shown) inside an actuator 18. By the actuator 18 controlling the position of the optical head 17, focusing control is performed. Specifically, immediately after an magneto-optical disk is loaded into the magneto-optical disk device $P_1$ or when data read/write is performed, the optical head 17 is allowed to approach the magneto-optical disk by the actuator 18, and if focusing is precisely done, the actuator 18 is controlled so as to maintain that state. If focusing is not done properly, the control is executed again, and the control is repeated for a set number of times until focusing becomes proper. Also, the optical head 17 is equipped with a coil for forming magnetism (not shown) other than the objective lens 17a.

Next, the cleaning action of the optical head 17 by the cleaner $C_1$ is explained.

First, when the cleaner $C_1$ is loaded into the loading section $L_1$ of the magneto-optical disk device $P_1$, the clamping disk 3 is held by the spindle 20. Also, the window 40a opens by the shutter 5 being moved by the opening mechanism (not shown) of the magneto-optical disk device $P_1$. Next, focusing control is started, wherein the objective lens 17a is allowed to approach the cleaner $C_1$ by the actuator 18. At this time even when the clamping disk 3 of the cleaner $C_1$ is rotated by the rotating spindle 20, the disk 1 is not rotated in this construction. Therefore, the objective lens 17 is allowed to approach the adhesive sheet 2 in a still state, and the adhesive sheet 2 and the objective lens 17a come into contact with each other. At this time, the adhesive sheet 2 is still and does not physically wipe the lens 17a. However, because the adhesive sheet 2 has appropriate adhesiveness, dust on the lens 17a adheres to the adhesive sheet 2. By this means, the objective lens 17a is cleaned. On the other hand, because the adhesive sheet 2 is made of silicone rubber, it is hard to reflect light. Hence, because the detector cannot detect returned light, focusing control continues afterwards. Hence, by the objective lens 17a being driven up and down repeatedly, the adhesive sheet 2 and the objective lens 17a come into contact with each other repeatedly, and cleaning of the objective lens 17a. is repeated. After the process is repeated several times, the magneto-optical disk device $P_1$ recognizes that an error in disk judgment has occurred and focusing control is ended. By this means, the optical head 17 equipped with the objective lens 17$a$ retreats to a specified position, and cleaning of the objective lens 17 is completed.

In this way, the adhesive sheet 2 does not rotate and only comes into contact with the objective lens 17$a$ in a still state. Hence, little horizontal frictional force occurs between them. Also, the adhesive sheet 2 made of silicone rubber has flexibility and becomes deformed elastically to fit with the objective lens 17 during contact, there is no excessive force such as that of the applied impact, and scratching the objective lens 17 and damaging other parts of the optical head 17 can be prevented. Furthermore, because the adhesive sheet 2 performs the function of retaining dust adhered to its surface, dust adhering to the adhesive sheet 2 does not adhere to the objective lens 17$a$ again. Because dust is not wiped away at high speed as in cleaning with a brush, dust is not scattered into the magneto-optical disk device $P_1$. Hence, dust can be prevented from remaining and accumulating inside the magneto-optical disk device $P_1$.

Figure 4:
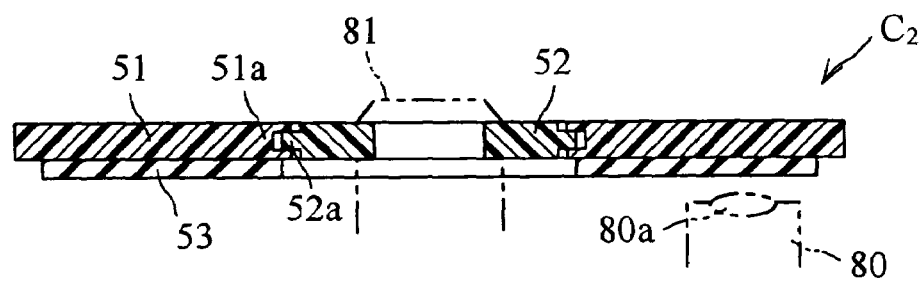
FIG. 4 is a cross-sectional view of another example of the cleaner for optical information processing devices related to the present invention.
Figure 5:
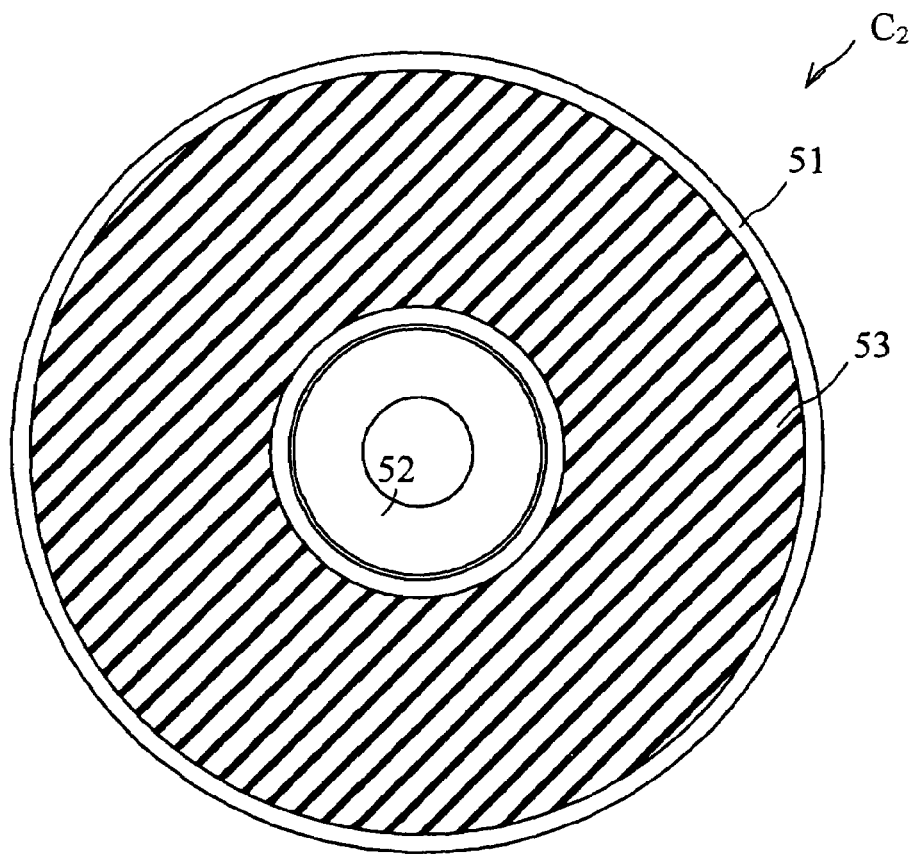
FIG. 5 is a bottom view of the cleaner for optical information processing devices shown in FIG. 4.

FIG. 4 and FIG. 5 show another example of the present invention. A cleaner $C_2$ in the present embodiment, unlike the cleaner $C_1$, for cleaning optical disk devices for reading/writing a medium having no cartridge, is constructed by being equipped with a cleaner disk 51, a clamping disk 52, and a ring-shaped adhesive sheet 53.

The adhesive sheet 53 is pasted so as to cover all tracks of one side of the disk 51. Also, as the material of the adhesive sheet 53, silicone rubber is adequate in the same way as in the embodiment example stated above.

The clamping disk 52 is fit into an opening installed at the center of the disk 51. A ring-shaped concave section 51$a$ on the inner circumference of the disk 51 and a ring-shaped convex section 52$a$ on the outer circumference of the clamping disk 52 fit with each other, by which the disk 51 and the clamping disk 52 are given a construction wherein they can rotate relative to each other in the track direction and do not disengage in the thickness direction.

Actions of the cleaner $C_2$ are explained next.

Once the cleaner $C_2$ is loaded into a loading section of an optical disk device, the clamping disk 52 is held by the spindle 81 of the optical disk device. An optical head 80 of the optical disk device is allowed to approach the cleaner $C_2$ from below the cleaner $C_2$ for performing focusing control. Afterwards, an objective lens 80$a$ installed on the optical head 80 and the adhesive sheet 53 come into contact with each other. At this time, the clamping disk 52 may occasionally be rotated by the spindle 81 rotating. However, the disk 51 and the clamping disk 52 are given a construction that allows them to rotate relative to each other. Also, the disk 51 comes into contact with the objective lens via the adhesive sheet 53. Hence, in the case, at least while the adhesive sheet 53 and the objective lens 80$a$ are in contact with each other, the disk 51 remains still, and only the clamping disk 52 rotates. Then, by dust on the objective lens 80$a$ adhering onto the adhesive sheet 53, the objective lens 80$a$ is cleaned. Hence, the same cleaning effect as in the embodiment form described above can be obtained.

Figure 6:
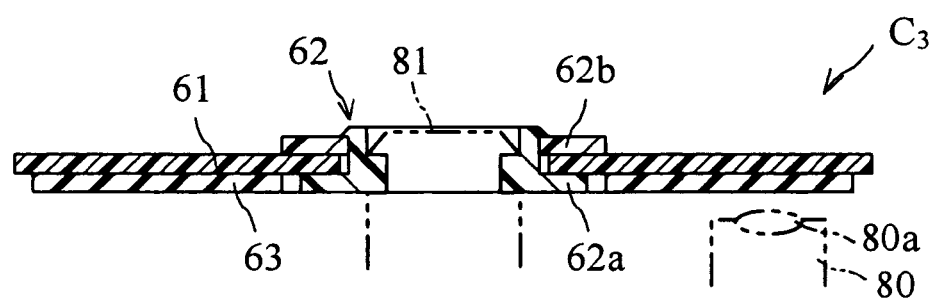
FIG. 6 is a cross-sectional view of another example of the cleaner for optical information processing devices related to the present invention.

Shown in FIG. 6 is another example of cleaner used for optical disk devices which read/write a medium having no cartridge.

A cleaner $C_3$ of the present embodiment form has a similar construction to the cleaner $C_2$, and is equipped with a disk 61, a clamping disk 62, and a ring-shaped adhesive sheet 63. The clamping disk 62 comprises a lower member 62$a$ and an upper member 62$b$. By a part of the lower member 62$a$ being fit into a hole installed on the upper member 62$b$ through a hole installed on the disk 61, the upper member 62$a$ and the lower member 62$b$ are combined. By such a construction, the disk 61 and the clamping disk 62 are given a construction wherein they can rotate relative to each other and do not disengage from each other in the thickness direction. According to such construction, the same effect as when cleaning with the cleaner $C_2$ can be obtained.

Figure 7:
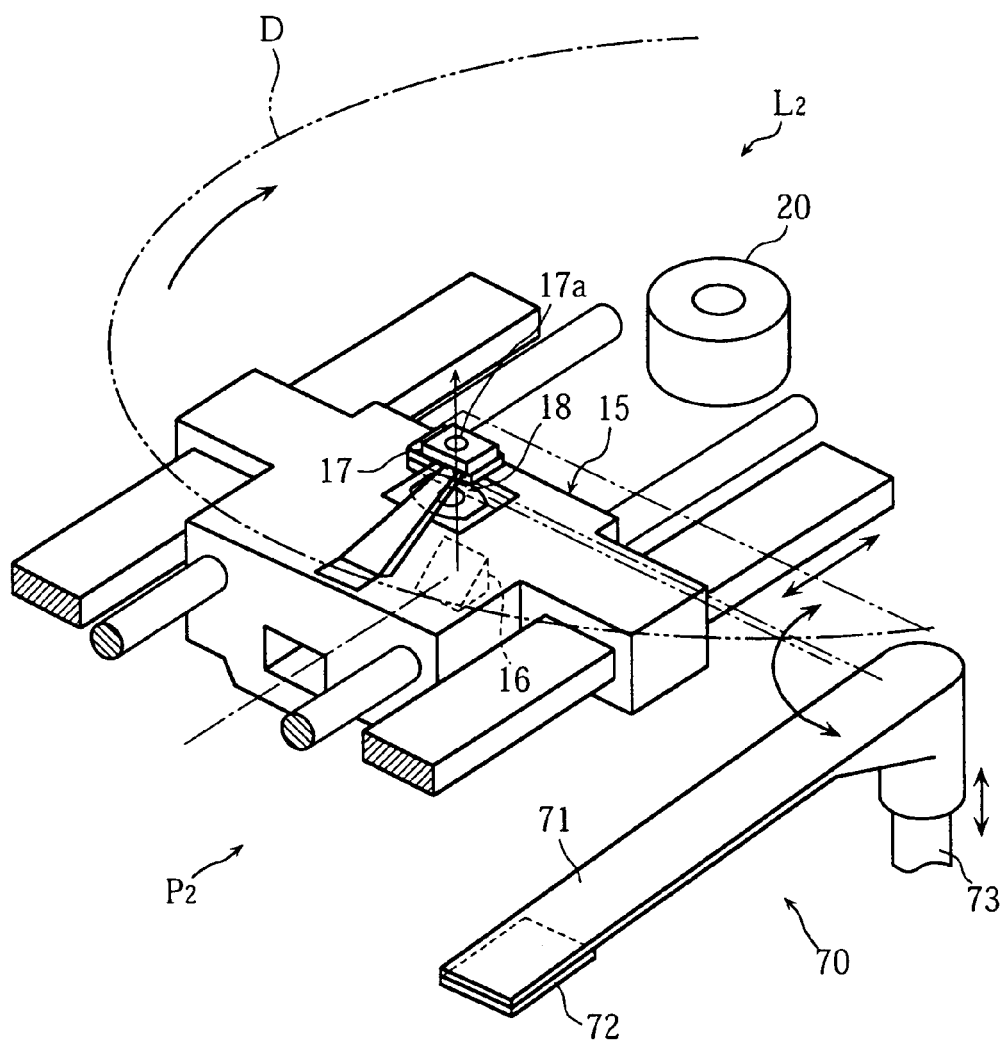
FIG. 7 is an outline oblique view of another example of the cleaner for optical information processing devices related to the present invention.

Shown in FIG. 7 is an example of the magneto-optical disk device related to the present invention.

A magneto-optical disk device $P_2$ is equipped with an optical unit (not shown), a carriage 15, an optical head 17, and a spindle 20 in the same way as in the magneto-optical disk device $P_1$. Furthermore, in addition to these, it is provided with a cleaner 70. The cleaner 70 is equipped with an arm 71, an adhesive-sheet 72, and a driving mechanism 73.

The adhesive sheet 72 is made of silicone rubber used in the embodiment example described above, which is pasted on the bottom face of the arm 71. The arm 71 is capable of rotating and ascending/descending by the driving mechanism 73.

The procedure of cleaning of the optical head 17 by the cleaner 70 is explained below.

When a magneto-optical disk D is loaded in a loading section $L_2$ of the magneto-optical disk device $P_2$, the arm 71 is retreated into a position which does not interfere with the magneto-optical disk D. In FIG. 7 the cleaner mechanism 70 in the retreated position is shown by a solid line. Cleaning is started after the magneto-optical disk D enters a state in which it is not loaded into the magneto-optical disk device $P_2$. First, the arm 71 is rotated by the driving mechanism 73 from the retreated position to a position immediately above the optical head 17. Next, the arm 71 is lowered by the driving mechanism 73 in the direction of the optical head 17. By so doing, the adhesive sheet 72 and objective lens 17$a$ of the optical head 17 come into contact with each other. Then, by dust on the objective lens 17$a$ adhering to an adhesive sheet 2, the objective lens 17$a$ is cleaned. Subsequently, after the arm 71 is lifted up by the driving mechanism 73 in the direction of moving away from the optical head 17, it is rotated to the retreated position.

According to such construction, a user can clean the optical head 17 without performing a work for loading the cleaner. Also, because dust is attached to the adhesive sheet 72 and does not fly scattered into the magneto-optical disk device $P_2$, dust can be prevented from accumulating inside the magneto-optical disk device $P_2$. Note that it may be given a construction in which the adhesive sheet 72 and the objective lens 17$a$ are put in contact with each other without lifting/lowering the arm 71 but by lifting/lowering the optical head 17.

Although silicone rubber is used as the raw material for the adhesive sheet in the embodiment, the present invention is not limited to this. In the present invention, the adhesive sheet can be constructed of a material which has rubbery elasticity other than silicone rubber.

In the present invention, a gel (e.g., trade mark Alpha Gel manufactured by Geltech Corp.) having silicone as the main raw material may be used as the raw material of the adhesive sheet. It is possible to equip this gel with enough adhesiveness to adhere dust onto the objective lens 17$a$ in the same way as silicone rubber used in the embodiment. Also, gels are flexible and deformable by external forces. Hence, even when this gel is put in contact with the objective lens 17$a$, it can be fit flexibly with the objective lens 17$a$. Because of this, having elasticity is not especially necessary in using a gel.

The invention claimed is:

1. A cleaner for an optical information processing device, comprising:
   a first disk mountable to a spindle of the optical information processing device;

a second disk supported around the first disk such that the first disk is allowed to rotate together with the spindle relative to the second disk, which is held stationary; and a cleaning contact member supported by the second disk for coming into contact with an optical head of the optical information processing device, wherein the contact member comprises an adhesive member including an adhesive surface to contact with the optical head of the optical information processing device.

2. The cleaner according to claim 1, wherein the adhesive member maintains a state which prevents it from moving in a direction intersecting with the contact direction when it comes into contact with the optical head.

3. The cleaner according to claim 1, wherein at least the surface portion of the adhesive member has rubbery elasticity.

4. The cleaner according to claim 1, wherein at least the surface portion of the adhesive member is made of a gel.

5. The cleaner according to claim 1, further comprising a cartridge for loading into a loading section of the optical information processing device, wherein the cartridge has a window allowing contact between the adhesive member and the optical head.

6. The cleaner according to claim 5, further comprising a shutter to open and close the window.

7. The cleaner according to claim 6, wherein the adhesive member is installed at a position facing the window inside the cartridge.

8. The cleaner according to claim 1, wherein a hole for inserting a spindle is formed on the center of the first disk.

9. The cleaner according to claim 1, wherein a hole is formed on the center of the second disk, and the whole or a part of the first disk fits rotatably in the hole.

* * * * *